United States Patent
Labhard

(10) Patent No.: US 9,092,554 B2
(45) Date of Patent: Jul. 28, 2015

(54) ALZHEIMERS SUPPORT SYSTEM

(75) Inventor: Michael Labhard, Lake Oswego, OR (US)

(73) Assignee: INTEL-GE CARE INNOVATIONS LLC, Roseville, CA (US)

(*) Notice: Subject to any disclaimer, the term of this patent is extended or adjusted under 35 U.S.C. 154(b) by 501 days.

(21) Appl. No.: 13/324,701

(22) Filed: Dec. 13, 2011

(65) Prior Publication Data

US 2013/0147899 A1    Jun. 13, 2013

(51) Int. Cl.
| | |
|---|---|
| H04M 11/04 | (2006.01) |
| G06F 19/00 | (2011.01) |
| G06Q 50/22 | (2012.01) |
| G06Q 10/10 | (2012.01) |
| A61B 5/00 | (2006.01) |

(52) U.S. Cl.
CPC .......... *G06F 19/3418* (2013.01); *G06Q 10/101* (2013.01); *G06Q 50/22* (2013.01); *A61B 5/002* (2013.01)

(58) Field of Classification Search
CPC .......... H04M 3/5166–3/5238; H04M 7/0012–7/0057; H04M 2201/42; H04M 2201/50; H04M 2203/40–2203/408; H04M 1/0027; H04M 1/2475; H04M 1/652; H04M 3/42391; H04M 3/5116; H04M 11/066; H04M 2201/40; H04M 2201/60; H04M 2242/04; G06F 19/3406–19/3425; G06Q 50/22; G06Q 10/101; A61B 5/002; A61B 5/08; A61M 16/0051; G08B 23/014; G08B 23/016; G08B 27/006
USPC ............ 348/14.01–14.16; 370/259–271, 370/351–357; 709/201–207, 217–248; 379/37–52, 67.1–88.28, 201.01, 379/202.01
See application file for complete search history.

(56) References Cited

U.S. PATENT DOCUMENTS

| | | | | |
|---|---|---|---|---|
| 4,695,903 | A | * | 9/1987 | Serap et al. .................... 386/359 |
| 5,181,018 | A | * | 1/1993 | Cowie et al. .................... 340/5.7 |
| 5,544,649 | A | * | 8/1996 | David et al. .................... 600/301 |
| 5,553,609 | A | * | 9/1996 | Chen et al. .................... 600/301 |
| 5,778,607 | A | * | 7/1998 | Edwards ......................... 52/79.1 |
| 5,861,806 | A | * | 1/1999 | Vories et al. .................. 340/555 |
| 5,902,234 | A | * | 5/1999 | Webb ............................ 600/300 |

(Continued)

OTHER PUBLICATIONS

Katherine Wild, et al., "Unobtrusive In-Home Monitoring of Cognitive and Physical Health: Reactions and Preceptions of Older Adults", NHI Public Access, J Appl Gerontol. 2008, total of 17 pages.

*Primary Examiner* — Hemant Patel
(74) *Attorney, Agent, or Firm* — Pillsbury Winthrop Shaw Pittman, LLP

(57) ABSTRACT

A system, method, and apparatus for reminding users with declining cognitive abilities that remote assistance from a caregiver is available and for providing a simplified way of requesting the assistance. The assistance may be provided through a videoconference on a patient assistance apparatus, which may comprise a screen, speaker, and microphone. The apparatus may remind the user when the user is present at or near the apparatus, which may be detected through a motion or proximity sensor. When the user is near, the apparatus may output an assistance inquiry message which proactively asks whether the user needs assistance. The apparatus may then receive a verbal or other form of inputted response. Based on the user's response, the apparatus may initiate a videoconference with the remote caregiver. The apparatus may also output a message inquiring whether the user is present, which may allow a remote caregiver to initiate a videoconference.

16 Claims, 3 Drawing Sheets

(56) References Cited

U.S. PATENT DOCUMENTS

| | | | |
|---|---|---|---|
| 5,987,519 A * | 11/1999 | Peifer et al. | 709/230 |
| 6,443,890 B1 * | 9/2002 | Schulze et al. | 600/300 |
| 7,185,282 B1 * | 2/2007 | Naidoo et al. | 715/718 |
| 7,242,421 B2 * | 7/2007 | Center et al. | 348/14.1 |
| RE42,288 E * | 4/2011 | Degioanni | 348/14.01 |
| 7,970,620 B2 * | 6/2011 | Brown | 705/2 |
| 8,447,654 B1 * | 5/2013 | Argue et al. | 705/16 |
| 2003/0023459 A1 * | 1/2003 | Shipon | 705/2 |
| 2005/0049898 A1 * | 3/2005 | Hirakawa | 705/5 |
| 2005/0086082 A1 * | 4/2005 | Braunstein et al. | 705/2 |
| 2005/0288737 A1 * | 12/2005 | Feliss et al. | 607/60 |
| 2006/0064319 A1 * | 3/2006 | Loevner | 705/2 |
| 2006/0106646 A1 * | 5/2006 | Squilla et al. | 705/3 |
| 2008/0294018 A1 * | 11/2008 | Kurtz et al. | 600/301 |
| 2009/0012373 A1 * | 1/2009 | Raij et al. | 600/300 |
| 2009/0083066 A1 * | 3/2009 | Bailey et al. | 705/2 |
| 2010/0286490 A1 * | 11/2010 | Koverzin | 600/301 |
| 2011/0267418 A1 * | 11/2011 | Galindo et al. | 348/14.04 |
| 2012/0130739 A1 * | 5/2012 | Crane | 705/3 |
| 2012/0143619 A1 * | 6/2012 | Routt | 705/2 |
| 2012/0166221 A1 * | 6/2012 | Phillips | 705/3 |
| 2012/0179479 A1 * | 7/2012 | Waterson et al. | 705/2 |
| 2012/0197662 A1 * | 8/2012 | Sun et al. | 705/2 |
| 2012/0212337 A1 * | 8/2012 | Montyne et al. | 340/501 |
| 2013/0060576 A1 * | 3/2013 | Hamm et al. | 705/2 |

* cited by examiner

ALZHEIMERS SUPPORT SYSTEM

TECHNICAL FIELD

Embodiments generally relate to providing remote assistance to patients or other care recipients experiencing cognitive decline, and more particularly to determining whether a patient needs assistance and to providing a simplified way for the patient to request assistance from a remote caregiver.

BACKGROUND

As the cost of medical care rises, providing in-home elderly care from caregivers who are required to make frequent house visits to an elderly or other patient may become prohibitively expensive. Remote care has thus become an important mode of patient care. It allows one caregiver to manage a large number of patients spread across a large geographic area.

Remote care, however, may still lack the resources to provide around-the-clock monitoring by remote caregivers of elderly patients. Such constant monitoring may also be regarded as intrusive. Rather than constantly monitor patients for conditions in which they might require assistance, some remote care systems instead attempt to predict when a patient requires assistance and dispatch assistance only when the systems infer that it is needed. The prediction or inference algorithms may be imperfect, however, and may dispatch assistance when it is unneeded or fail to detect a need for assistance.

Some remote care systems have relied on users to request assistance, such as through pushing a call button, which may generate a signal that is transmitted through a network to a remote caregiver. However, patients with declining cognitive abilities, such as those suffering from Alzheimer's Disease, may have difficulty remembering what they are doing and whether that activity or condition requires assistance. Such patients may also fail to recall how to request assistance. A responsive remote care system for patients with declining cognitive abilities is needed.

SUMMARY OF THE INVENTION

One aspect of this invention relates to providing assistance to patients with Alzheimer's Disease or other conditions leading to declining cognitive abilities. Assistance may be provided through a video conference with a remote care giver, who may diagnose a patient's medical condition, identify medication for the patient, instruct the patient on how to use certain medical equipment or how to perform certain daily living activities, or provide other forms of assistance. The patient may conduct the video conference with a patient assistance apparatus located in his or her home. The apparatus may have a screen, a speaker, and a microphone. A system that reminds patients of the availability of remote assistance and facilitates requesting of the remote assistance is thus provided.

In some embodiments, the apparatus may proactively survey the patient on the need for assistance. Because a patient with Alzheimer's may forget how to request assistance or fail to discern that he or she needs assistance, the apparatus may remind the patient of the availability of remote assistance and how to obtain the assistance. For example, the apparatus may remind the patient by displaying an assistance inquiry message. The message may be an audio message asking whether the patient needs assistance or a text message displayed on a screen. In some embodiments, outputting of the message may be triggered by presence of the patient at or near the apparatus housing the screen and/or speaker. The presence may be detected by a motion or proximity sensor incorporated into the apparatus or by an external motion or proximity sensor. The apparatus may present simple ways for the patient to respond. For example, the assistance inquiry message may instruct the patient to answer yes or no, may present a yes button and no button on the screen, or perform a combination thereof. Touch sensing technology on the screen may capture a user response inputted on the screen, while a microphone may capture a verbal response. If the user response is, for example, a "yes," the apparatus may initiate a video conference with a remote caregiver. For example, the apparatus may communicate with a remote care center, and may establish a videoconference connection with a videoconferencing server at the remote care center. The apparatus thus reminds Alzheimer's patients that remote assistance is available, and further reminds them how to obtain the assistance.

In some embodiments, the assistance inquiry message may be outputted at predetermined intervals. For example, if the patient is constantly at or near the apparatus, the apparatus may periodically present an assistance inquiry message to remind the patient to assess whether he or she has a condition or is performing an activity that requires assistance. If the apparatus does not receive a response after a predetermined amount of time, it may infer that the patient does not require assistance. The predetermined threshold may be increased each time no response is received. The apparatus may dispatch assistance if no response is received after a predetermined number of inquiries.

In some embodiments, the apparatus may facilitate initiation of a videoconference by a remote caregiver. For example, a remote caregiver wishing to check up on a patient may submit a presence inquiry message to the apparatus. The message may be a recorded audio message, a text message, or a presence inquiry command that is part of a communication protocol between the remote caregiver's videoconferencing application and the apparatus. In response to receiving the presence inquiry message, the apparatus may attempt to determine whether the patient is present at or near the apparatus. In one example, if a presence sensor in or communicating with the apparatus indicates that the patient is near or at the apparatus, it may simply transmit the presence indication to the remote caregiver. If the presence sensor indicates that the patient is not near the apparatus, or if the patient is near the apparatus but his or her attention is focused away from the apparatus, the apparatus may output the recorded audio message, may generate an audio message from the text message or from the presence inquiry command, may display the text message on the screen, or perform a combination thereof. The apparatus may further include an alert device, such as a LED, light bulb, strobe, beeper, or any other device that may attract the attention of the patient. For example, the apparatus may flash the LED, light bulb, strobe, or emit periodic sounds on the beeper along with outputting the presence inquiry message. In some embodiments, the patient may be presented with an option to indicate that he or she is present and an option to indicate that he or she is not present. In some embodiments, lack of any user response after a predetermined interval may lead to an inference that he or she is not present. A patient thus does not need to affirmatively indicate that he or she is not present, but may simply ignore the presence inquiry message. After the apparatus receives an indication that the patient is present, it may transmit the indication to the remote caregiver, or may directly establish a videoconference connection with the remote caregiver.

In some embodiments, the apparatus may present videoconference options to the patient. For example, the apparatus may present a message asking whether the patient desires to enable only an audio portion of the video conference, or may present specific caregivers from whom the patient may select for a videoconference consultation.

BRIEF DESCRIPTION OF THE DRAWINGS

The various advantages of the embodiments of the present invention will become apparent to one skilled in the art by reading the following specification and appended claims, and by referencing the following drawings, in which:

DETAILED DESCRIPTION

One aspect of this invention is directed toward an apparatus for reminding a user of the availability of remote assistance and providing a simple way of requesting the assistance. The user may be a patient suffering from Alzheimer's Disease or other forms of cognitive decline, and may thus forget that he or she has a condition or activity that warrants assistance. The patient may forget how to request that assistance, or even that assistance is available. The apparatus may thus proactively present messages to the patient asking whether he or she needs assistance, and remind the patient how to request assistance. For example, the apparatus may instruct the patient to respond to the assistance inquiry message by giving a verbal answer or inputting an answer on a touch screen. If the patient does need assistance, the apparatus may provide it through a videoconference with a remote caregiver.

Figure 1:
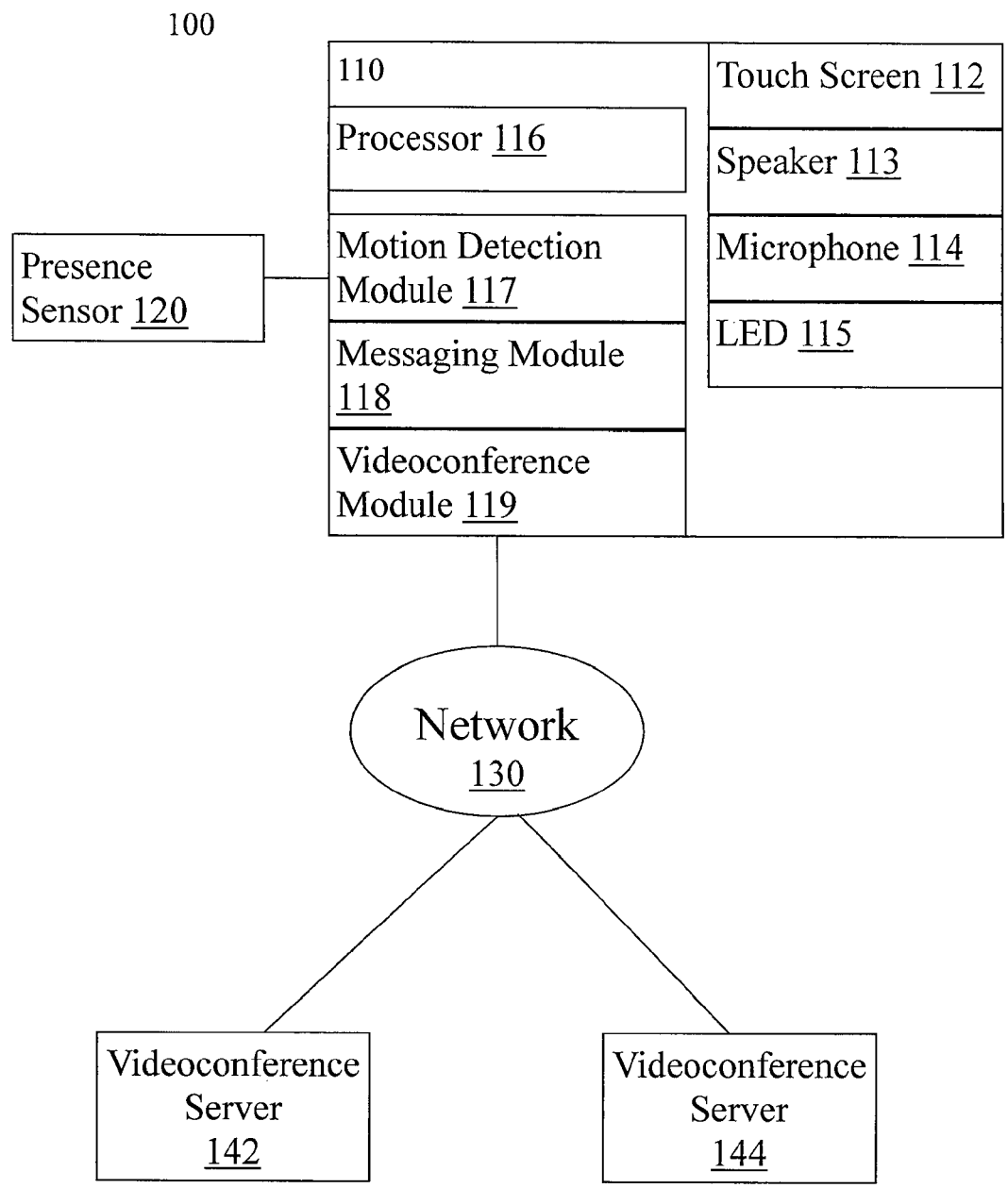
FIG. 1 illustrates an example remote care system that provides a simplified way for users with declining cognitive abilities to request assistance from a remote caregiver.

FIG. 1 illustrates a patient assistance system 100 for detecting the patient's need for assistance, such as assistance through a videoconference with the remote caregiver. The example system shown in FIG. 1 may include a patient assistance apparatus 110 and a presence sensor 120. System 100 may be located in the vicinity of the patient, such as in the patient's home, hospital, nursing home, or other care facility. The system may communicate with one or more remote videoconference servers 142, 144 through network 130. Network 130 may be part of, for example, the Internet. Server 142 may be located at one patient care facility that is remote from system 100, while server 144 may be located at a different patient care facility that is also remote from system 100.

In some embodiments, presence sensor 120 may be part of patient assistance apparatus 110. In some embodiments, presence sensor 120 may be external to patient assistance apparatus 110. In such embodiments, presence sensor 120 may communicate with a communication interface of apparatus 110, such as a USB® interface, an IEEE 1394 (Firewire) interface, a RS 232 (serial) interface, a Bluetooth® interface, an IEEE 802.11 (Wi-Fi) interface, or any combination thereof. In some embodiments, presence sensor 120 may be part of patient assistance apparatus 110. Presence sensor 120 may comprise a proximity sensor, such as an infrared sensor, or a motion sensor, such as a passive infrared (PIR) or microwave sensor, or any other sensor configured to detect the patient's presence at or near apparatus 110.

In some embodiments, patient assistance apparatus 110 may include a touch screen 112, speaker 113, microphone 114, a LED 115, one or more processors, such as processor 116, and a motion detection module 117, a messaging module 118, and a videoconference module 119. The modules may comprise logic circuits, software instructions stored in a storage device, or any combination thereof. In some embodiments, patient assistance apparatus 110 may have other user interface devices, such as a mouse and/or a keyboard. In some embodiments, apparatus 110 may include a screen that is not touch sensitive. In some embodiments, the one or more processors may communicate to the screen, speaker, or microphone through an electrical connection, which may be formed from interconnects, transistors, and other electrical components. In some embodiments, the one or more processors may instead communicate with the screen, speaker, or microphone through a wireless connection. In some embodiments, apparatus 110 may have no LED, or may have an alternative alert device, such as a light bulb, a strobe, a beeper, or any other device that may be activated (e.g., lit and/or flashed) to attract the patient's attention.

In some embodiments, the modules may contain instructions that may be executed by the one or more processors, such as by processor 116. Motion detection module 117, when executed by the one or more processors, may receive and process data from presence sensor 120. Module 117 may perform any data analysis, such as signal processing, to determine whether a patient or any other user is approaching or present at or near apparatus 110. Messaging module 118, when executed, may display a message on touch screen 112, on speaker 113, or any combination thereof. Messaging module 118 may include instructions for displaying a message on a screen, converting text to an audio message, converting an audio message to text, or any combination thereof. Videoconference module 119, for example, may establish a videoconference connection with a remote caregiver. The module may establish a connection with, for example, videoconference server 142 or videoconference server 144.

Figure 2:
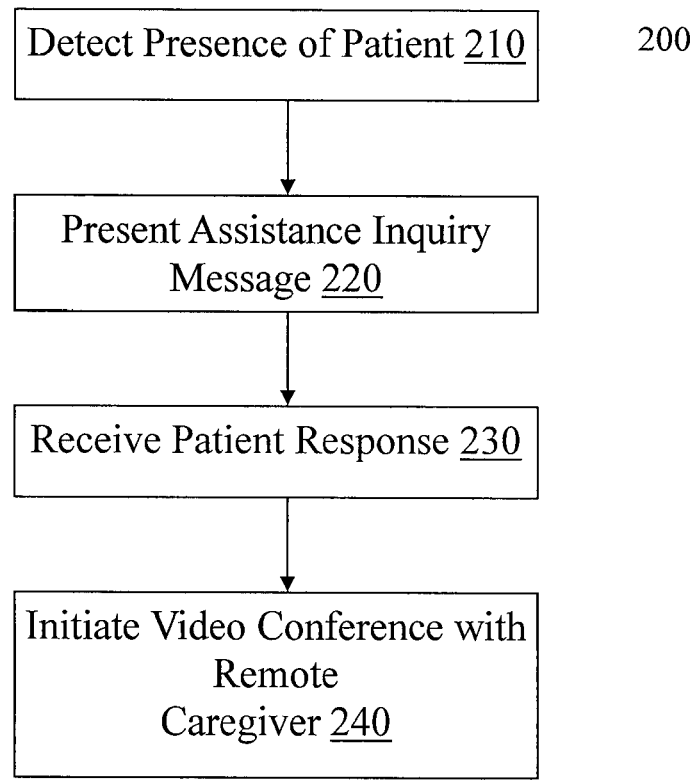
FIG. 2 illustrates an example method for surveying patients on whether they require assistance from a remote caregiver.

FIG. 2 illustrates a method 200 for offering assistance to a patient. Assistance may be offered as the patient passes by a patient assistance apparatus, such as apparatus 110. Because the patient may have a cognitive decline that causes him or her to forget what he or she is doing, forget that he or she has a medical condition, forget his or her physical surroundings, or forget the availability of assistance, the apparatus may generate a visual, audio, or tactile output that reminds the patient that he or she can request assistance from a remote caregiver via the apparatus. At operation 210, presence of the patient at or near the apparatus may be detected. Motion detection, such as that performed by module 117, proximity detection, or a combination thereof may be used to detect the patient's presence. For example, the apparatus may incorporate a PIR or ultrasound sensor that detects a moving object approaching the apparatus, or may receive an indication of user presence from a nearby pressure sensor or infrared sensor. In some embodiments, a degree of proximity may also be detected. For example, data from the ultrasound sensor and the PIR sensor may be combined to detect how far the patient is from the apparatus.

At operation 220, an assistance inquiry message may be generated. The message may be generated by messaging module 118 or any other computing circuit configured to present a message to a user. Generating the assistance inquiry message may include retrieving a predefined message from a storage device. The message may be a text message or a graphic displayed on a screen, an audio message outputted from a speaker, or any combination thereof. For example, a text or audio message of "Do you need Assistance?" may be outputted at operation 210. In that example or another example, a graphic representation of a caregiver may be presented on the screen with a question mark beside it. In some embodiments, a more detailed message may be generated. For example, a text message may ask whether the patient needs medical assistance or daily living activity assistance. In some embodiments, selection of the level of detail of the assistance inquiry message may be based on a degree of proximity of the patient. If a patient is relatively far from, for example, a patient assistance apparatus, a simple message such as "Do you need assistance?" may be outputted from the apparatus. If the patient is relatively close, a more detailed message may be outputted. For example, a more detailed message may ask whether the patient needs medical assistance or assistance in performing a daily living activity. In this or another example, the more detailed message may comprise a sequence of messages. A first message in the sequence may ask whether the patient needs medical assistance. Based on the response received from the patient, a second message in the sequence may ask whether the medical assistance relates to an emergency. Based on the response received from the patient (e.g., "NO"), a third message in the sequence may ask whether the patient needs assistance related to medication or related to medical diagnostics equipment (e.g., with a blood glucose monitor, or with a heart rate monitor).

In some embodiments, if assistance is provided through a videoconference, assistance inquiry message may present options for the videoconference. For example, the message may ask "Would you like an audio-only consultation?" or "If you know the name of the person with whom you would like to talk to, please say his or her name now." The assistance inquiry message may thus provide simple instructions on how the patient may respond and request assistance. In this or another example, the assistance inquiry message include an audio, "Answer Yes or No" message. In the same or another example, assistance inquiry message may include a visual message displayed on a touch screen. The visual message may comprise, for example, a button labeled "Yes" and a button labeled "No."

At operation 230, a response from the patient may be received, such as by apparatus 110. The response may be received from a microphone, from a touch screen, a keyboard, a mouse, or any other user input device. For example, sound information captured by the microphone may be processed to determine whether a "Yes" or "No" was spoken by the patient. In this or another example, user input information at the touch screen may be processed to determine whether the patient had pressed the "Yes" button or the "No" button. The form of the user input may be dynamically detected, so that the patient can flexibly respond verbally or by inputting at the touch screen. In some embodiments, a lack of response may be treated as a "No." For example, after a predetermined threshold amount of time in which no patient response is received, outputting of the assistance inquiry message may be stopped. The time threshold may be increased each time no response is received, and may be reset when a patient response is received. In some embodiments, after a threshold amount of time or threshold number of times in which no patient response is received, an indication of patient unresponsiveness may be transmitted to a remote caregiver, who may then attempt to contact the patient if such the unresponsiveness appears abnormal.

At operation 240, a video conference may be initiated with a remote caregiver, such as by videoconference module 119 of apparatus 110. The videoconference module may establish a videoconference connection directly with a caregiver's computing device, such as when the caregiver is a family member, or may first establish a videoconference connection with a videoconference server used by a care center. The videoconference may include an audio portion, a video portion, or some combination thereof. For example, if the patient indicated in a response that he or she would like an audio-only consultation, then the video portion may be disabled for the particular videoconference session. Through the videoconference, a caregiver may provide assistance such as identifying medication for the patient, examining the patient's surroundings for safety issues, visually instructing the patient on medical equipment use, or providing other forms of assistance.

Figure 3:
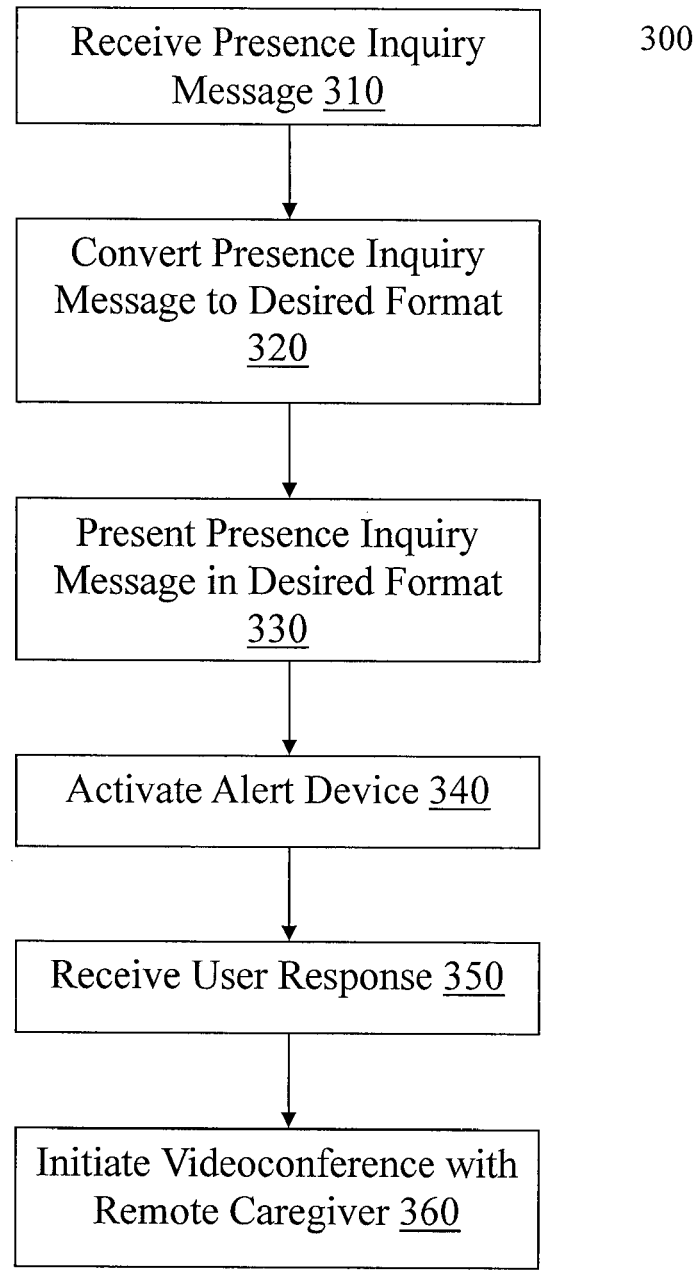
FIG. 3 illustrates an example method that allows a remote caregiver to initiate a videoconference session in which assistance can be provided.

FIG. 3 illustrates a method for a caregiver to initiate a videoconference session with a patient. The caregiver at a remote facility may not know whether the patient is near a videoconference apparatus, such as apparatus 110, or whether he or she is otherwise available. The caregiver may attempt to schedule a videoconference with the patient, but procedures for scheduling a videoconference may be too complicated or onerous for the patient. The caregiver may instead inquire whether the patient is present at or near a videoconferencing apparatus, such as apparatus 110. At operation 310, a presence inquiry message may be received from the caregiver. In some embodiments, the presence inquiry message may be a message recorded by the caregiver, such as "Martha, are you there?" or "Are you available?" In some embodiments, the presence inquiry message may be a presence inquiry command provided in a videoconference protocol.

At operation 320 and 330, the presence inquiry message may be presented in a desired format and presented to the patient. A desired format may be based on, for example, a default option or a user profile. The profile may indicate, for example, that the patient has poor hearing, in which case visual messages are more desired, or that the patient has poor eyesight, in which case audio messages are more desired. At operation 320, the presence inquiry message may be converted to the desired text, audio, or other format. For example, a presence inquiry command may be converted to a natural language text format. In this or another example, a text message may be converted to an audio message through a text-to-speech engine, or an audio message may be converted to a text message through a voice recognition engine. The converted presence inquiry message may then be presented on a speaker, screen, or any combination thereof.

In some embodiments, operations 320 and 330 may work together with a presence sensor, such as presence sensor 170. For example, upon receiving a presence inquiry message, the presence sensor may be checked for whether the patient is near. If the patient is near, the proximity information may be transmitted to the caregiver without performing operations 320 and 330. If the patient is not near, operation 320 and 330 may be performed to attract the patient's attention and draw the patient toward a videoconference apparatus, such as apparatus 110.

At operation 340, an alert device may be activated to further attract the patient's attention. For example, a LED, light bulb, or a strobe may be flashed, or sounds may be emitted from a beeper. In some embodiments, a screen, such as screen 112, may flash bright colors to attract the patient's attention.

At operation 350, the patient's response may be received. The presence inquiry message may have instructed the patient on how to respond. For example, the presence inquiry message may include an audio or text message instructing the patient to "Answer Yes or No" or "Press Yes or No." In some embodiments, the presence inquiry may time out after a threshold amount of time. Thus, if a patient does not wish to conduct a videoconference, he or she may actively respond "No" or may simply ignore the presence inquiry.

At operation 360, a videoconference between the remote caregiver and the patient may be initiated if the patient responded that he or she was present. As discussed earlier, the videoconference may comprise an audio portion, a video portion, or any combination thereof.

Embodiments of the present invention are applicable for use with all types of semiconductor integrated circuit ("IC") chips. Examples of these IC chips include but are not limited to processors, controllers, chipset components, programmable logic arrays (PLA), memory chips, network chips, and the like. In addition, in some of the drawings, signal conductor lines are represented with lines. Some may be thicker, to indicate more constituent signal paths, have a number label, to indicate a number of constituent signal paths, and/or have arrows at one or more ends, to indicate primary information flow direction. This, however, should not be construed in a limiting manner. Rather, such added detail may be used in connection with one or more exemplary embodiments to facilitate easier understanding of a circuit. Any represented signal lines, whether or not having additional information, may actually comprise one or more signals that may travel in multiple directions and may be implemented with any suitable type of signal scheme, e.g., digital or analog lines implemented with differential pairs, optical fiber lines, and/or single-ended lines.

Example sizes/models/values/ranges may have been given, although embodiments of the present invention are not limited to the same. Arrangements may be shown in block diagram form in order to avoid obscuring embodiments of the invention, and also in view of the fact that specifics with respect to implementation of such block diagram arrangements are highly dependent upon the platform within which the embodiment is to be implemented, i.e., such specifics should be well within purview of one skilled in the art. Where specific details (e.g., circuits) are set forth in order to describe example embodiments of the invention, it should be apparent to one skilled in the art that embodiments of the invention can be practiced without, or with variation of, these specific details. The description is thus to be regarded as illustrative instead of limiting.

Those skilled in the art will appreciate from the foregoing description that the broad techniques of the embodiments of the present invention can be implemented in a variety of forms. Therefore, while the embodiments of this invention have been described in connection with particular examples thereof, the true scope of the embodiments of the invention should not be so limited since other modifications will become apparent to the skilled practitioner upon a study of the drawings, specification, and following claims.

I claim:

1. A patient assistance apparatus, comprising:
   one or more processors configured to
      receive an indication of presence of a user distance to the patient assistance apparatus from an infrared proximity sensor,
      output an assistance inquiry message, based on the user distance, on a user output device in response to receiving the indication of user presence,
      receive a user response from a user input device,
      determine whether assistance is needed based on the user response, and
      establish a videoconference connection with a remote caregiver if assistance was determined to be needed.

2. The patient assistance apparatus of claim 1, wherein the user output device comprises a touch screen and a speaker, and wherein the user input device comprises the touch screen and a microphone.

3. The patient assistance apparatus of claim 2, wherein the patient assistance apparatus further comprises an alert device electrically connected to the one or more processors, wherein the one or more processors are configured to activate the alert device.

4. The patient assistance apparatus of claim 3, wherein the alert device comprises a LED, a light bulb, a strobe, a beeper, or any combination thereof, and wherein activating the alert device comprises flashing the LED, light bulb, or strobe, outputting a plurality of high-pitched sounds on the beeper, or any combination thereof.

5. The patient assistance apparatus of claim 2, wherein the one or more processors are configured to display a plurality of colors, one color at one time, on the touch screen.

6. The patient assistance apparatus of claim 2, wherein the one or more processors are further configured to
   receive a presence inquiry message from the remote caregiver,
   determine whether the presence inquiry message is in an audio format,
   convert the received presence inquiry message to an audio format if it is not in an audio format,
   output the presence inquiry message in the audio format on the speaker,
   receive a second user response from the microphone or from the touch screen, and
   establish the videoconference connection with the remote caregiver in response to receiving the second user response,
   wherein the presence inquiry message from the remote caregiver is received before the indication of user presence is received from the infrared proximity sensor.

7. A patient assistance system, comprising:
   a patient assistance apparatus comprising:
      a touch screen configured to receive user input,
      a microphone configured to receive user input,
      a speaker, and
      one or more processors electrically connected to the touch screen, the microphone, and the speaker; and
   an infrared proximity sensor configured to detect a user at or near the patient assistance apparatus, wherein the infrared proximity sensor is part of the patient assistance apparatus or is external to the patient assistance apparatus, and
   wherein the one or more processors are configured to
      receive an indication of presence of a user distance to the patient assistance apparatus from the infrared proximity sensor,
      output an assistance inquiry message, based on the user distance, on the touch screen or on the speaker in response to receiving the indication of user presence,
      receive a user response from the touch screen or from the microphone,
      determine whether assistance is needed based on the user response, and
      establish a videoconference connection with a remote caregiver if assistance was determined to be needed.

8. The patient assistance system of claim 7, wherein the patient assistance apparatus further comprises an alert device electrically connected to the one or more processors, wherein the one or more processors are configured to activate the alert device.

9. The patient assistance system of claim 8, wherein the alert device comprises a LED, a light bulb, a strobe, a beeper, or any combination thereof, and wherein activating the alert device comprises flashing the LED, light bulb, or strobe, outputting a plurality of high-pitched sounds on the beeper, or any combination thereof.

10. The patient assistance system of claim 7, wherein the one or more processors are configured to display a plurality of colors, one color at one time, on the touch screen.

11. A patient assistance method implemented by one or more processors, the method comprising:
   receiving an indication of presence of a user distance to a patient assistance apparatus from an infrared proximity sensor;
   outputting an assistance inquiry message, based on the user distance, on a touch screen or a speaker of the patient assistance apparatus in response to receiving the indication of user presence from the infrared proximity sensor;
   receiving a user response from the touch screen or from a microphone;
   determining that the user needs assistance based on the user response; and
   establishing a videoconference connection with a remote caregiver.

12. The patient assistance method of claim 11, further comprising activating an alert device.

13. The patient assistance method of claim 12, further comprising displaying a plurality of colors, one color at one time, on the touch screen.

14. A patient assistance method implemented by one or more processors, the method comprising:
   receiving a presence inquiry message from a remote caregiver;
   determining a presence inquiry output format based on user profile;
   converting the received presence inquiry message to the determined user-desired output format;
   confirm a presence of a user distance to a user apparatus using a proximity sensor associated with the user apparatus;
   outputting the converted presence inquiry message, based on the user distance, on a screen or on a speaker associated with the user apparatus in the user-desired output format to the user;
   receiving a user response from a microphone or a touch screen associated with the user apparatus; and
   establishing a videoconference connection with the remote caregiver in response to receiving the user response.

15. The patient assistance method of claim 14, further comprising activating an alert device in response to receiving the presence inquiry message to alert the user of the received presence inquiry message.

16. The patient assistance method of claim 15, wherein the alert device comprises a LED, a light bulb, a strobe, a beeper, or any combination thereof, and wherein activating the alert device comprises flashing the LED, light bulb, or strobe, outputting a plurality of high-pitched sounds on the beeper, or any combination thereof.

* * * * *